(12) United States Patent
Rapier et al.

(10) Patent No.: US 7,074,977 B2
(45) Date of Patent: Jul. 11, 2006

(54) REACTOR AND PROCESS FOR CONVERTING ALKANES TO ALKENES

(75) Inventors: Charles R. Rapier, Billings, MT (US);
Daniel P. Holderman, Spring, TX (US); Zhen Chen, Bend, OR (US); Shang Y. Chen, Edmond, OK (US); Steven R. McDonald, Greensboro, NC (US); Lisa M. Budin, Ponca City, OK (US); Sriram Ramani, Ponca City, OK (US); Joe D. Allison, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 0 days.

(21) Appl. No.: 10/731,748

(22) Filed: Dec. 9, 2003

(65) Prior Publication Data

US 2005/0124841 A1    Jun. 9, 2005

(51) Int. Cl.
*C07C 5/333*    (2006.01)

(52) U.S. Cl. ............ 585/324; 585/658; 585/652; 585/653

(58) Field of Classification Search ........ 585/324, 585/658, 652, 653
See application file for complete search history.

(56) References Cited

U.S. PATENT DOCUMENTS

| | | | |
|---|---|---|---|
| 3,855,330 A | 12/1974 | Mendelsohn et al. | |
| 3,904,703 A | 9/1975 | Lo et al. | |
| 4,739,124 A | 4/1988 | Ward | |
| 5,439,859 A | 8/1995 | Durante et al. | |
| 5,563,314 A | 10/1996 | Agaskar et al. | |
| 5,625,111 A | 4/1997 | Astbury et al. | |
| 6,395,944 B1 * | 5/2002 | Griffiths et al. | ............ 585/324 |
| 6,433,234 B1 | 8/2002 | Griffiths et al. | |

FOREIGN PATENT DOCUMENTS

WO    WO 01/83405 A1    11/2001

OTHER PUBLICATIONS

U.S. Department of Energy, "Hot Oxygen Injection Into the Blast Furnace", Steel Project Fact Sheet, Feb. 2001, 2 p.
A. S. Bodke et al.; "Oxidative Dehydrogenation of Ethane at Millisecond Contact Times: Effect of $H_2$ Addition," Journal of Catalysis, vol. 191, pp. 62–74 (2000).

* cited by examiner

*Primary Examiner*—Thuan D Dang
(74) *Attorney, Agent, or Firm*—Conley Rose P.C.

(57) ABSTRACT

The invention relates to a reactor comprising two reaction zones and processes for the production of alkenes from alkanes. A first reaction zone includes a combustion catalyst, and a second reaction zone comprises a heating zone in thermal contact with the first reaction zone. One process comprises generating heat and an effluent by the combustion of a fuel with oxygen in the first reaction zone; passing an alkane feed through the heating zone of the second reaction zone such that the alkane feed absorbs a sufficient amount of the heat generated in the first reaction zone to initiate the conversion of alkanes to alkenes in the second reaction zone. In other embodiments, the effluent comprises oxygen, and the second reaction zone excludes a catalyst; alternatively, the effluent is substantially free of oxygen, and the second reaction zone comprises a supplemental oxygen feed and may or may not include a catalyst.

67 Claims, 2 Drawing Sheets

REACTOR AND PROCESS FOR CONVERTING ALKANES TO ALKENES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

This invention relates to the field of alkane conversion to alkenes and more specifically to the field of oxidative conversion of alkanes to alkenes in a two-zone reactor.

2. Background of the Invention

There is currently a significant interest in various types of hydrocarbon processing reactions. One such class of reactions involves the chemical conversion of natural gas, a relatively low value reactant, to higher value products. Natural gas comprises several components, including alkanes. Alkanes are saturated hydrocarbons—e.g., compounds consisting of hydrogen (H) and carbon (C)—whose molecules contain carbon atoms linked together by single bonds. The principal alkane in natural gas is methane; however, significant quantities of longer-chain alkanes such as ethane ($CH_3CH_3$), propane ($CH_3CH_2CH_3$) and butane ($CH_3CH_2CH_2CH_3$) are also present Unlike even longer-chain alkanes, these so-called lower alkanes are gaseous under ambient conditions.

The interest in the chemical conversion of the lower alkanes in natural gas stems from a variety of factors. First, vast reserves of natural gas have been found in remote areas where no local market exists. There is great incentive to exploit these natural gas formations because natural gas is predicted to outlast liquid oil reserves by a significant margin. Unfortunately, though, the transportation costs for the lower alkanes are generally prohibitive, primarily because of the extremely low temperatures needed to liquefy these highly volatile gases for transport. Consequently, there is considerable interest in techniques for converting methane and other gaseous hydrocarbons to higher value products and/or more easily transportable products at the remote site. A second factor driving research into commercial methods for chemical conversion of lower alkanes is their abundant supply at many refineries and the relatively few commercially-viable means of converting them to more valuable products.

Several hydrocarbon processing techniques are currently being investigated for the chemical conversion of lower alkanes. One such technique involves the conversion of methane to higher chain-length alkanes that are liquid or solid at room temperature. This conversion of methane to higher hydrocarbons is typically carried out in two steps. In the first step, methane is converted with an oxidant to produce a mixture of carbon monoxide and hydrogen known as synthesis gas or syngas. In a second step, the syngas is converted to liquid hydrocarbon fuels and solid hydrocarbon waxes using the Fischer-Tropsch synthesis. The high molecular weight waxes thus produced provide an ideal feedstock for hydrocracking, which ultimately yields jet fuel, gasoline, high-decane diesel fuel, or blending stocks for such fuels, particularly superior high decane value diesel fuel.

Another important class of hydrocarbon processing reactions relates to the production of olefins from alkanes. Olefins have traditionally been produced from alkanes by fluid catalytic cracking (FCC) or steam cracking, depending on the size of the alkanes. Heavy olefins are herein defined as containing at least five carbon atoms and are produced by FCC. Light olefins are defined herein as containing two to four carbon atoms and are predominantly produced by steam cracking. Olefins can also be generated from low molecular weight alkanes by dehydrogenation reactions. In a dehydrogenation process, alkanes can be dehydrogenated to produce alkenes.

Alkenes, or olefins, are higher value chemicals than their corresponding alkanes. This is true, in part, because alkenes are important feedstocks for producing various commercially useful materials such as detergents, high-octane gasolines, pharmaceutical products, plastics, synthetic rubbers and viscosity additives. In the commercial production of plastics, elastomers, manmade fibers, adhesives, and surface coatings, a tremendous variety of polymers are used. By far the most important industrial polymers are polymerized olefins, which comprise virtually all commodity plastics. Ethylene, a raw material in the production of polyethylene, is the one of the most abundantly produced chemicals in the United States and cost-effective methods for producing ethylene are of great commercial interest.

Olefins are unsaturated hydrocarbons (compounds containing hydrogen [H] and carbon [C]) whose molecules contain one or more pairs of carbon atoms linked together by a double bond. The olefins are classified in either or both of the following ways: (1) as cyclic or acyclic (aliphatic) olefins, in which the double bond is located between carbon atoms forming part of a cyclic (closed-ring) or an open-chain grouping, respectively, and (2) as monoolefins, diolefins, triolefins, etc., in which the number of double bonds per molecule is, respectively, one two, three, or some other number. Hence, olefins are highly desired for the production of plastics.

Generally, olefin molecules are commonly represented by the chemical formula $CH_2$=CHR, where C is a carbon atom, H is a hydrogen atom, and R is an atom or pendant molecular group of varying composition. The composition and structure of R determines which of the huge array of possible properties will be demonstrated by the polymer. More specifically, acyclic monoolefins have the general formula $C_nH_{2n}$, where n is an integer. Acyclic monoolefins are rare in nature but are formed in large quantities during the cracking of petroleum oils to gasoline. The lower monoolefins, i.e., ethylene, propylene, and butylene, have become the basis for the extensive petrochemicals industry. Most uses of these compounds involve reactions of the double bonds with other chemical agents. Acyclic diolefins, also known as acyclic dialkenes, or acyclic dienes, with the general formula $C_nH_{2n-2}$, contain two double bonds; they undergo reactions similar to the monoolefins. The best-known dienes are butadiene and isoprene, used in the manufacture of synthetic rubber.

Olefins containing two to four carbon atoms per molecule are gaseous at ordinary temperatures and pressure; those containing five or more carbon atoms are usually liquid at ordinary temperatures. Additionally, olefins are only slightly soluble in water.

The FCC process is a catalytic thermal process, while steam cracking is a direct, non-catalytic dehydrogenation process. FCC and steam cracking are known to have drawbacks. For example, both processes are endothermic, meaning that heat energy must be supplied to drive the reaction.

In addition, in FCC, coke forms on the surface of the catalyst during the cracking processes, covering active sites and deactivating the catalyst. During regeneration, the coke is burned off the catalyst to restore its activity and to provide heat needed to drive the cracking This cycle is very stressful for the catalyst; temperatures fluctuate between extremes as coke is repeatedly deposited and burned off. Furthermore, the catalyst particles move at high speed through steel reactors and pipes, where wall contacts and interparticle contacts are impossible to avoid. The conversion of alkanes to alkenes in both FCC and steam cracking processes may be via multi reaction steps but overall reaction can be explained as a dehydrogenation reaction. One example of such a dehydrogenation reaction is the conversion of ethane to ethylene (Reaction 1):

$$C_2H_6 + \text{Heat} \rightarrow C_2H_4 + H_2 \quad (1)$$

FCC and steam cracking units are large and expensive because the FCC unit requires a catalyst regenerator and its catalysts use typically precious metals, and because the steam cracking unit requires furnaces to generate heat energy for the conversion of alkane to alkene. Recently, there has been increased interest in oxidative dehydrogenation (ODH) as an alternative to FCC and steam cracking for the production of olefins. In ODH, alkanes are dehydrogenated in the presence of an oxidant such as molecular oxygen, typically in a short contact time reactor containing an ODH catalyst. The net ODH reaction, for example as depicted in [Reaction 2] for the conversion of ethane and oxygen to ethylene and water.

$$C_2H_6 + \tfrac{1}{2} O_2 \rightarrow C_2H_4 + H_2O + \text{Heat} \quad (2)$$

Because the exothermic combustion provides most of the heat necessary to drive the endothermic dehydrogenation reaction, ODH is a substantially autothermal process and requires no or very little energy to sustain the reaction. Energy savings over traditional, endothermal processes (FCC and steam cracking) can be significant if the heat produced with ODH is recaptured and recycled. In addition, the capital costs for olefin production via ODH are significantly less than with the traditional processes, because ODH uses simple fixed bed reactor designs and high volume throughput.

Although ODH involves the use of a catalyst, which is referred to herein as an ODH catalyst, and is therefore literally a catalytic dehydrogenation, ODH is distinct from what is normally called "catalytic dehydrogenation" in that the former involves the use of an oxidant and the latter does not.

Oxidative dehydrogenation of hydrocarbons (ODH) with short contact time reactors (SCTR) is an alternative to traditional steam cracking and non-oxidative dehydrogenation processes. During an ODH reaction, an oxidant, preferably molecular oxygen, is co-fed with saturated hydrocarbons, optionally balanced with an inert gas, at a gas hourly space velocity (GHSV) of about 20,000 to 10,000,000 hr$^{-1}$. The oxidant may be fed as pure molecular oxygen, air, oxygen-enriched air, oxygen mixed with a diluent, and so forth. Oxidant in the desired amount may be added in the feed to the dehydrogenation zone. The contact time of the reactants with the catalyst is typically in the 1 to 200 ms range. The reaction pressure range is typically between 0.8 bar and 5 bars (about 80 kPa–500 kPa), and the reaction temperature is typically between 800 and 1,100° C.

Successful commercialization of an ODH process depends on the efficacy of the catalyst. In other words, successful commercial scale operation for catalytic hydrocarbon processing depends upon high hydrocarbon feedstock conversion at high throughput and with acceptable selectivity for the desired reaction products. In turn, the yield and selectivity of an ODH catalyst system are affected by several factors. One of the most important of these factors is the catalyst composition, which significantly affects not only the yields and product distributions but also the overall economics of the process. Unfortunately, few catalysts offer both the performance and cost necessary for economical large-scale industrial use.

Catalyst cost is one of the most significant economic considerations in ODH processes. Non-oxidative dehydrogenation reactions frequently employ relatively inexpensive iron-oxide based catalysts. In contrast, ODH catalysts typically utilize relatively expensive precious metals, e.g., platinum, as promoters that assist in the combustion reaction. In order to reduce catalyst costs, therefore, it is desirable to maximize the effectiveness of the catalyst composition, or minimizing its use.

Consequently, there is a need for an alkane-to-alkene conversion process with an improved conversion and selectivity. Further needs include an improved reactor system for the oxidative conversion of alkanes to alkenes. Additional needs include an improved reactor and process for the management of heat produced in the alkene production process. In addition, needs include a reduction in hydrogen co-product in the alkene production process by the oxidative conversion of alkanes.

BRIEF SUMMARY OF SOME OF THE PREFERRED EMBODIMENTS

The invention relates to a reactor and processes comprising two reaction zones for the production of alkenes from alkanes. A first reaction zone comprises the combustion of a fuel to generate heat and combustion products, such as carbon dioxide and water, and a second reaction zone comprises the oxidative conversion of at least one alkane to form an alkene product.

In an embodiment, the first reaction zone employs a stoichiometric excess of oxygen such that at least a portion of the oxygen fed to the first reaction zone does not react with the fuel. The unconverted oxygen is passed to the second reaction zone, which preferably does not contain a catalytic material, such that it facilitates the non-catalytic conversion of at least one alkane to an alkene. In another embodiment, the first reaction zone consumes substantially all of the supplied oxygen, such that substantially no oxygen from the first reaction zone is passed to the second reaction zone. A supplemental oxygen feed is then added to the second reaction zone so as to facilitate the oxidative conversion of at least one alkane to an alkene. The conversion of an alkane to alkene may be non-catalytic or may be done in the presence of a catalyst.

A need in the art is addressed in one embodiment by a reactor for producing alkenes from alkanes. The reactor for producing alkenes from alkanes comprises a first reaction zone comprising a catalytic bed, wherein the first reaction zone is operated at conditions sufficient to generate heat by the combustion of a fuel; a first feed inlet connected to one end of the first reaction zone, wherein the first reaction zone feed inlet is suitable for introducing a first reaction zone feed comprising the fuel and an oxygen-containing gas to the first reaction zone; a first reaction zone outlet connected to another end of the first reaction zone, wherein the first reaction zone outlet is suitable for passing a first reaction zone effluent; a second reaction zone comprising a heating zone, wherein the heating zone is in thermal contact with the first reaction zone to allow at least a fraction of the heat generated in the first reaction zone to be transferred to the second reaction zone, wherein the second reaction zone is operated at conditions sufficient to generate an alkene product; an alkane feed inlet connected to the heating zone of the second reaction zone, wherein the alkane feed inlet is suitable for introducing an alkane feed to the heating zone; and a second reaction zone outlet connected to another end of the second reaction zone, wherein the second reaction zone outlet is suitable for passing a second reaction zone effluent comprising the alkene product.

In another embodiment, the invention comprises a process for the oxidative conversion of alkanes to alkenes. The process comprises generating heat and an effluent by the combustion of a fuel with oxygen in a first reaction zone; passing an alkane feed through a heating zone of a second reaction zone such that the alkane feed absorbs sufficient amount of the heat generated in the first reaction zone to initiate the conversion of alkanes to alkenes in the second reaction zone. In some embodiments, the effluent comprises oxygen, and the second reaction zone excludes a catalyst; alternatively, the effluent is substantially free of oxygen, and the second reaction zone comprises a supplemental oxygen feed, which may or may not include a catalyst.

In another embodiment, the invention comprises a process for the production of alkenes from alkanes. The process comprises feeding a first zone feed to a first reaction zone having a combustion catalyst, wherein the first zone feed comprises an oxygen-containing gas and a fuel; contacting the first zone feed with the combustion catalyst under conditions sufficient to combust at least a portion of the fuel so as to form a first reaction zone effluent having less than about 1,000 ppm oxygen; feeding the combustion zone effluent to a second reaction zone; introducing an oxygen-containing feed and an alkane feed to the second reaction zone; and reacting at least a portion of the alkane feed with oxygen in the second reaction zone at conditions sufficient to form an alkene product.

In a further embodiment, the invention comprises a process for the production of alkenes from alkanes. Such a process comprises feeding a first zone feed to a first reaction zone having a combustion catalyst, wherein the first zone feed comprises an oxygen-containing gas and a fuel; contacting the first zone feed with the combustion catalyst under conditions sufficient to combust at least a portion of the fuel so as to produce heat and a combustion zone effluent; feeding an alkane feed to a second reaction zone, wherein at least a portion of the second reaction zone is in thermal contact with the first reaction zone, and wherein the alkane feed absorbs a sufficient amount of the heat produced in the first reaction zone to initiate the conversion of at least one alkane to an alkene in the second reaction zone, and converting at least a portion of the alkane feed so as to form an alkene product.

In another embodiment, the invention comprises a process for the production of alkenes from alkanes. Such a process comprises feeding a first zone feed to a first reaction zone having a combustion catalyst, wherein the first zone feed comprises an oxygen-containing gas and a fuel; contacting the first zone feed with the combustion catalyst under conditions sufficient to combust at least a portion of the fuel so as to form a first reaction zone effluent containing at least 1,000 ppm oxygen; providing an alkene production zone comprising a heating zone in thermal contact with the first reaction zone, wherein the alkene production zone is substantially free of catalytic metal; passing the first reaction zone effluent to the alkene production zone; introducing an alkane feed to the alkene production zone; heating the alkane feed through the heating zone by heat transfer from the first reaction zone to the heating zone; and reacting at least a portion of the alkane feed with oxygen in the alkene production zone so as to form an alkene product.

In additional embodiments, the reactor comprises a short contact time reactor. In other embodiments, the alkene comprises ethylene.

It will therefore be seen that a technical advantage of the present invention includes an improved reactor and process for the production of alkenes from alkanes that overcomes the problem of consuming part of the alkane feed to produce heat. The alkane feed is fed separately to the reactor from the combustion feed. Further advantages include a more efficient management of heat produced in the alkene production process. In addition, advantages include reducing the hydrogen co-product that is common in many alkene production processes.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
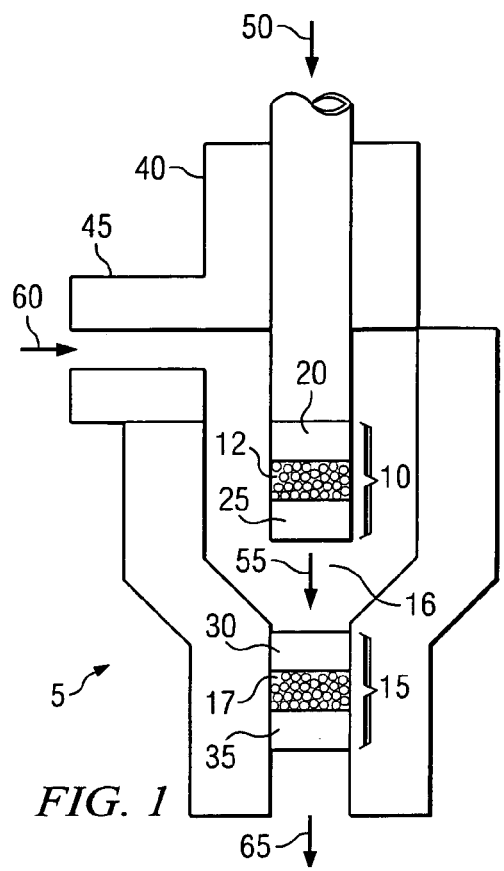
FIG. 1 illustrates a two-zone alkene production reactor having two reaction zones, each zone comprising a catalyst.

FIG. 1 illustrates a reactor 5 comprising a combustion zone 10 and an alkene production zone 15. Reactor 5 can comprise a short contact time reactor (SCTR), a catalytic fixed bed reactor, and a tube-shell reactor, preferably reactor 5 comprises a SCTR.

Combustion zone 10 comprises a combustion catalyst bed 12 having a catalyst that is active in the combustion of an alkane feed. The combustion catalyst comprises any suitable metals that exhibit catalytic activity in the combustion of alkanes. A preferable combustion catalyst includes chromium, copper, manganese, iron, platinum, palladium, rhodium, ruthenium, iridium, cobalt, nickel, osmium, cerium, lanthanum, chromium oxide, copper oxide, manganese oxide, iron oxide, cobalt oxide, nickel oxide, tin oxide, samarium oxide, or combinations thereof.

The combustion catalyst can further comprise one or more promoters. Promoters are well known in the art, and the present invention may include any suitable promoter for improving the performance of the combustion catalyst. Preferable promoters for the combustion catalyst include rhodium, ruthenium, iridium, platinum, palladium, osmium, chromium, or combinations thereof. More preferably, the promoters comprise platinum, palladium, chromium, or combinations thereof. The combustion catalyst should comprise any suitable promoter concentration from about 0.001 to about 10 percent by weight of the catalyst. When the combustion catalyst comprises palladium as the promoter, the catalyst has a palladium content preferably from about 0.001 percent to about 1 percent by weight of the catalyst, and more preferably from about 0.05 percent to about 0.2 percent by weight of the catalyst. When the combustion catalyst comprises platinum as the promoter, the catalyst has a platinum content preferably from about 0.01 percent to about 8 percent by weight of the catalyst, and more preferably from about 0.5 percent to about 7 percent by weight of the catalyst. When the combustion catalyst comprises chromium as the promoter, the catalyst has a chromium content preferably from about 0.01 percent to about 5 percent by weight of the catalyst, and more preferably from about 0.5 percent to about 3 percent by weight of the catalyst.

In addition, the combustion catalyst may further comprise a support. Catalyst supports are well known in the art, and the combustion catalyst may comprise any suitable support for use in combustion zone 10. Without limiting the scope of the invention, the support used in the combustion catalyst can include a support comprising any inorganic oxide that is stable (i.e., unreactive) at the operating temperature of combustion zone 10. The support can be in any suitable shape including foam, monolith, gauze, noodles, spheres, pills or the like, for operation at the desired gas velocities with minimal back pressure. A combustion catalyst combination may be separate and distinct catalyst structures (each of which has particular catalytic properties) or may be a single catalyst structure comprising two or more catalytically active components on a support material.

Combustion zone 10 preferably comprises a combustion shield 20 and a combustion floor 25. Shields are well known in the art, and combustion shield 20 can comprise any suitable shield for reducing energy loss and/or preventing the reaction from backing up the feed. Combustion shield 20 can comprise any suitable material, preferably alumina. Floors for catalytic beds are well known in the art, and combustion floor 25 can comprise any suitable floor for supporting combustion catalyst bed 12 and combustion shield 20. Combustion floor 25 can comprise any suitable material, such as a refractory material, preferably alumina.

Alkene production zone 15 comprises an alkene production catalyst bed 17 having a catalyst that is active in the dehydrogenation of alkanes. The alkene production catalyst comprises one or more suitable metals that exhibit catalytic activity in an alkene production process. Preferably, the alkene production catalyst comprises at least one base metal. As used herein, "base metal" includes metals selected from the group consisting of metals from Groups 2, 4–7, 11–15 of the Periodic Table of the Elements (according to the New Notation WUPAC Form as illustrated in, for example, the *CRC Handbook of Chemistry and Physics, 82$^{nd}$ Edition*, 2001–2002; with such reference being the standard herein and throughout), scandium, yttrium, actinium, iron, cobalt, nickel, their oxides and combinations thereof. The base metal preferably includes a metal or metal oxide from Groups 2, 4–7, 11–13 of the Periodic Table of the Elements or any combination thereof. More preferably, the base metal is selected from the group consisting of manganese, chromium, tin, copper, gold, their corresponding oxides and combinations thereof. When present, the base metal is preferably present at a base metal loading of between about 0.5 and about 20 weight percent of the alkene production catalyst, more preferably between about 1 and about 12 weight percent of the alkene production catalyst, and still more preferably between about 2 and about 6 weight percent of the alkene production catalyst.

The alkene production catalyst may further comprise at least one promoter. Promoters are well known in the art, and the present invention may include any suitable promoter for improving the performance of the catalyst. Preferable promoters in the alkene production catalyst include one or more metals of Groups 8, 9, and 10 of the Periodic Table. More preferably, the promoter in the alkene production catalyst comprises platinum, palladium, iridium, rhodium, ruthenium, or any combinations thereof. The promoter metal is preferably present at a promoter metal loading of between about 0.005 and about 0.20 weight percent of the alkene production catalyst, more preferably between 0.005 and 0.1 weight percent of the alkene production catalyst, still more preferably between 0.005 and 0.075 weight percent of the alkene production catalyst, and yet still more preferably between 0.005 and 0.05 weight percent of the alkene production catalyst. The molar ratio of the base metal to the promoter metal is preferably about 10 or higher, more preferably about 15 or higher, still more preferably 20 or higher, and yet still more preferably about 25 or higher.

In addition, the alkene production catalyst may further comprise supports. Catalyst supports are well known in the art, and the alkene production catalyst may comprise any suitable support for use in alkene production zone 15. In preferred embodiments, the alkene production catalyst comprises a support. Without limiting the scope of the invention, the alkene production catalyst support can include zirconia, magnesium stabilized zirconia, zirconia stabilized alumina, yttrium stabilized zirconia, calcium stabilized zirconia, alumina, titania, silica, magnesia, niobia, vanadia, nitrides, silicon nitride, carbides, silicon carbide, cordierite, cordieritealpha alumina, zircon mullite, spodumene, aluminasilica magnesia, zircon silicate, sillimanite, magnesium silicates, zircin, petalite, carbon black, calcium oxide, barium sulfate, silicaalumina, alumina-zirconia, alumina-chromia, alumina-ceria, or combinations thereof. More preferably, the refractory support comprises alumina, zirconia, silicon nitride, magnesium oxide or combinations thereof. Suitable oxides include metastable and stable phases of the foregoing, including for example, gamma and alpha alumina and other alumina phases, any of which may be referred to as "alumina." When alumina is used as support, alumina is preferably in the form of alphaalumina (α-alumina); however, the other forms of alumina have also demonstrated satisfactory performance. The support may be modified, stabilized, or pretreated in order to achieve the proper structural stability desired for sustaining the operating conditions of the reaction in which the supported catalysts are utilized.

The support used in the alkene production catalyst can be in the shape of wire gauzes, porous monoliths, discrete particles, and the like, preferably particles. Monoliths typically comprise any singular piece of material of continuous manufacture such as pieces of metal or metal oxide, foam materials, or honeycomb structures. Two or more such catalyst monoliths may be stacked in the catalyst zone of the reactor if desired. For example, the catalyst can be structured as, or supported on, a refractory oxide "honeycomb" straight channel extrudate or monolith, made of cordierite or mullite, or other configuration having longitudinal channels or passageways permitting high space velocities with a minimal pressure drop. Such configurations are known in the art and described, for example, in *Structured Catalysts and Reactors*, A. Cybulski and J. A. Moulijn (Eds.), Marcel Dekker, Inc., 1998, p. 599–615 (Ch. 21, X. Xu and J. A. Moulijn, "Transformation of a Structured Carrier into Structured Catalyst"), which is hereby incorporated herein by reference in its entirety. The terms "discrete" particles, as used herein, refer to supports in the form of divided materials such as granules, beads, pills, pellets, cylinders, trilobes, spheres, other rounded shapes, other manufactured configurations and the like. Alternatively, the divided material may be in the form of irregularly shaped particles. An alkene production catalyst combination may be separate and distinct catalyst structures (each of which has particular catalytic properties) or may be a single catalyst structure comprising at least one catalytically active component on a support material.

Suitable alkene production catalysts are disclosed in co-owned published U.S. patent applications No. 2003-0040655 and 2003-0065235, each of which is herein incorporated by reference in its entirety.

Alkene production zone 15 preferably comprises a shield 30 and a floor 35. Shields are well known in the art, and shield 30 can comprise any suitable shield for reducing energy loss and/or preventing the reaction from backing up the feed. Shield 30 may also facilitate distribution of feed gas. Shield 30 can comprise any suitable material, such as a refractory material, preferably alumina. Floors for catalytic beds are well known in the art, and floor 35 can comprise any suitable floor for supporting alkene production catalyst bed 17 and shield 30. Floor 35 can comprise any suitable material, preferably alumina Shield 30 and floor 35 preferably comprise porous material so as to minimize pressure drop. For example, ceramic foam pieces of alumina with 60 or less pores per linear inch would be suitable.

Optionally, reactor 5 comprises preheater 40 and/or preheater 45. Preheaters are well known in the art, and preheaters 40 and 45 comprise any suitable preheaters for use in reactor 5. Examples of suitable preheaters include band (electric) heaters, steam heaters, heat exchangers, and/or fired heaters.

The following describes an exemplary application of the present invention as illustrated in FIG. 1. Combustion feed 50 is fed to combustion zone 10 and contacted with the combustion catalyst in combustion catalyst bed 12. Combustion feed 50 is a gas comprising an oxygen-containing gas and a fuel. The fuel comprises hydrogen, carbon monoxide, C1–C4 alkanes such as methane, C1–C4 alkenes, naphtha, natural gas, syngas, or mixtures thereof, preferably methane. Without limitation, examples of suitable oxygen-containing gases include substantially pure oxygen ($O_2$); air; $O_2$-enriched air; $O_2$ diluted with an non-reactive gas such as nitrogen; any recycle stream or effluent stream from another unit, which may comprise a significant $O_2$ content, and which may have been sent through a separation unit in order to concentrate its $O_2$ content. In alternative embodiments, the fuel comprises any gas or liquid hydrocarbon. Combustion feed 50 should have a fuel-to-oxygen ratio between 1:10 and 20:1. The oxygen-containing gas and the fuel can be present in combustion feed 50 in any ratio of oxygen-containing gas to fuel that is suitable for combustion of the oxygen, as long as the oxygen is in sufficient amount to stoichiometrically assure combustion of the fuel. Combustion feed 50 is preferably pre-heated in preheater 40 before being fed to combustion zone 10. Preferably, combustion feed 50 is pre-heated to temperatures up to about 600° C. and more preferably from about 200° C. to about 400° C. The preheated combustion feed 50 is fed to combustion zone 10 in which the fuel is combusted or partially combusted. Combustion zone 10 can operate at any conditions sufficient for the combustion or partial combustion of the fuel. For instance, combustion zone 10 operates at a pressure of 10 psig or more, preferably operates at pressures of about 45 psig or more, more preferably at about 100 psig or more, and still more preferably between about 300 and 550 psig. The gas hourly space velocity (GHSV) of combustion zone 10 is preferably from about 10,000 $hr^{-1}$ to about 1,000,000 $hr^{-1}$, and more preferably from about 10,000 $hr^{-1}$ to about 100,000 $hr^{-1}$. In addition, the gas phase temperature in combustion zone 10 should be from about 200° C. to about 2,000° C., preferably from about 200° C. to about 1,000° C., more preferably from about 300° C. to about 650° C. The combustion zone effluent 55 comprises heat generated in combustion zone 10. Preferably, combustion zone effluent 55 exits combustion zone 10 at temperatures from about 200° C. to about 1,600° C., more preferably at temperatures from about 200° C. to about 1,000° C., and still more preferably at temperatures from about 300° C. to about 650° C. Components in combustion zone effluent 55 may include water, oxides of carbon such as carbon dioxide or carbon monoxide, hydrogen, carbon, some residual oxygen, or combinations thereof. Preferably, a substantial portion of the oxygen in combustion feed 50 is consumed in combustion zone 10 with combustion zone effluent 55 comprising less than 1,000 ppm oxygen, more preferably less than 500 ppm oxygen, still more preferably less than 100 ppm oxygen. In some embodiments combustion feed 50 is substantially free of oxygen. The complete conversion of oxygen in combustion feed 50 is typically due to the selection of a molar fuel-to-oxygen ratio in combustion feed 50 such that the fuel is in stoichiometric excess. If the stoichiometric fuel-to-oxygen molar ratio for complete combustion of fuel with oxygen to generate water, carbon dioxide or both is equal to "x," then the molar ratio of fuel to oxygen in combustion feed 50 should be greater than "x" in order to produce a combustion zone effluent 55 with a minimal oxygen content. In this particular embodiment, it is desirable that alkane feed 60 also comprise an oxygen-containing gas. When alkane feed 60 comprises both an alkane and oxygen and is heated by thermal contact with combustion zone 10, it is expected that at least a portion of the alkane may be converted to an alkene by a non-catalytic reaction in the heat exchange (heating) zone, especially if the heat transfer is sufficient for alkane feed 60 to reach a temperature sufficient to initiate such reaction between the alkane and oxygen before the heated alkane feed 60 exits heating zone 16. In other embodiments, combustion feed 50 may comprise more than 1,000 ppm oxygen. This may be achieved when the molar ratio of fuel-to-oxygen in combustion feed 50 is lower than "x" (stoichiometric fuel-to-oxygen molar ratio for complete combustion) in order to produce combustion zone effluent 55 with a residual oxygen content.

In alternative embodiments (not illustrated), combustion zone 10 comprises a syngas catalyst bed (not illustrated) instead of combustion catalyst bed 12. In such alternative embodiments, the fuel in combustion feed 50 reacts with the oxygen to produce carbon monoxide, optionally carbon dioxide, and hydrogen. Heat is produced by the exothermic selective oxidation reaction of the fuel with oxygen to produce carbon monoxide and hydrogen. Syngas catalysts are well known in the art, and any syngas catalysts suitable for producing a syngas product from a fuel (preferably comprising a hydrocarbon gas) and oxygen may be used. Preferably, platinum, palladium, nickel, iridium, ruthenium, rhodium, or mixtures thereof are used. More preferably, nickel, iridium, ruthenium, rhodium, or mixtures thereof are used. It is to be understood that any suitable support and promoters may be used with the syngas catalysts. Suitable syngas catalysts are disclosed in co-owned published U.S. patent application No. 2002-0115730, which is herein incorporated by reference in its entirety.

Alkane feed 60 is fed to reactor 5. The flow rate of alkane feed 60 to reactor 5 can be any suitable rate. Preferably, alkane feed 60 is fed to reactor 5 at a flow ratio of alkane feed 60 to combustion feed 50 of 1:1 to 10:1, more preferably 1.2:1 to 4:1, and most preferably 1.4:1 to 2:1. Alkane feed 60 is a gas comprising at least one alkane. Alkane feed 60 can comprise any alkanes, preferably ethane. In alternative embodiments, alkane feed 60 also comprises an oxygen-containing gas. Without limitation, examples of suitable oxygen-containing gases include substantially pure oxygen ($O_2$); air; $O_2$-enriched air; . $O_2$ diluted with an inert gas such as nitrogen; any recycle stream or effluent stream from another unit, which may comprise a significant $O_2$ content, and which may have been sent through a separation unit in order to concentrate its $O_2$ content. The alkane to oxygen molar ratio can be any suitable ratio for use in reactor 5, preferably from about 1.6:1 to about 10:1, more preferably from about 2:1 to about 4:1. Alkane feed 60 can be fed at ambient temperature to reactor 5 or can be pre-heated in preheater 45 before being fed to alkene production zone 15. The alkene production catalyst composition, the alkane feed 60 composition, and the amount of combustion heat transferred to alkane feed 60 are such that oxidative dehydrogenation promoting conditions can be maintained with a feed preheat temperature of about 600° C. or less. Preferably, the alkene production catalyst composition, the alkane feed 60 composition, and the amount of combustion heat transferred to alkane feed 60 are such that alkene production promoting conditions can be maintained with a preheat temperature of about 400° C. or less. In preheater 45, alkane feed 60 is pre-heated to temperatures from about 20 to about 600° C., more preferably from about 20 to about 500° C., and most preferably from about 100 to about 400° C. Preferably, pre-heating alkane feed 60 allows for less combustion feed 50 to be fed to reactor 5. In some embodiments, the heat of combustion provides entirely the heat required to pre-heat alkane feed 60 to the desirable preheat temperature for initiating the oxidative dehydrogenation of the alkane.

Alkane feed 60 is co-fed with combustion zone effluent 55 to alkene production zone 15 and contacted with the alkene production catalyst in catalytic bed 17 to produce alkenes by oxidative conversion of the alkanes that are present in the two feeds. Alkane feed 60 and combustion zone effluent 55 can be fed separately or mixed. Alkene production zone 15 can operate at any conditions sufficient to initiate conversion of at least one alkane to an alkene. For instance, alkene production zone 15 preferably operates at pressures of about 2 psig or more, more preferably at about 45 psig or more, still more preferably at about 90 psig or more, and most preferably between about 100 psig and about 500 psig. The gas hourly space velocity (GHSV) of alkene production zone 15 is preferably from about 10,000 $hr^{-1}$ to about 10,000,000 $hr^{-1}$, and more preferably from about 50,000 $hr^{-1}$ to about 4,000,000 $hr^{-1}$. In addition, the reaction temperature in alkene production zone 15 is preferably from about 600° C. to about 1,200° C., more preferably from about 700° C. to about 1,000° C. Reactor effluent 65 comprises the product of alkene production zone 15. At least a portion of the alkanes are dehydrogenated and converted to alkenes. Reactor effluent 65 typically comprises alkenes, alkanes, CO, $CO_2$, and $H_2$. Reactor effluent 65 may also comprise small amounts of alkynes. It is to be understood that the reactor conditions and other parameters can be controlled to obtain any desired alkane conversion and alkene selectivity. The preferable alkene is ethylene. Preferred alkane conversion is at least about 40 percent, and the alkene selectivity is at least about 30 percent. More preferably, the alkane conversion is at least about 60 percent, and the alkene selectivity is at least about 50 percent. Still more preferably, the alkane conversion is at least about 70 percent, and the alkene selectivity is at least about 55 percent.

Figure 2:
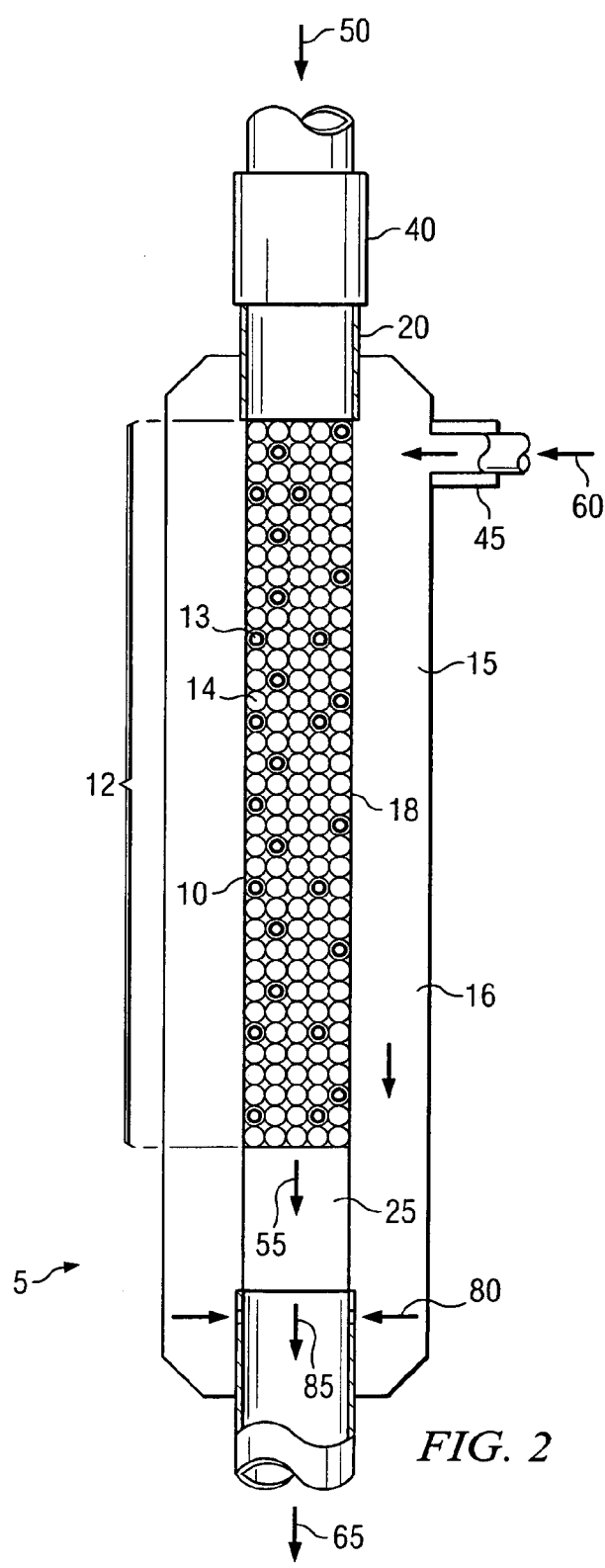
FIG. 2 illustrates a two-zone alkene production reactor having a first reaction zone comprising a diluted catalytic bed and a second reaction zone comprising a heating zone.

FIG. 2 illustrates an embodiment of the invention wherein alkene production zone 15 does not comprise an alkene production catalyst bed 17. Instead, alkene production catalyst bed 17 is optional and if used is located downstream of alkene production zone 15. Alternatively, in lieu of alkene production catalyst bed 17, a bed comprising a refractory material (such as an inorganic refractory oxide like alumina, zirconia, and the like) and that is substantially free of catalytic metal may be placed downstream of combustion zone 10. In the embodiment of FIG. 2, combustion catalyst bed 12 is elongated over that shown in FIG. 1. The lengthening of combustion catalyst bed 12 is correlated on the catalyst bed dilution. Combustion catalyst bed 12 comprises catalyst structures 13 and a diluent material 14. The amount of catalyst dilution in combustion catalyst bed 12 may be selected depending on the desired exit temperature of the gas and/or on the maximum gas temperature increase across combustion catalyst bed 12. It is expected that a high dilution ratio of diluent material-to-catalyst should result in lowering the gas phase temperature within combustion catalyst bed 12, as well as the rate in which the gas phase temperature increases from the inlet to the outlet of combustion catalyst bed 12. Combustion catalyst bed 12 may comprise a dilution weight ratio based on diluent material-to-catalyst between about 1:2 to about 10:1, preferably between about 1:1 to about 8:1; still more preferably at about 3:1. The diluent material may be a refractory material, such as silica, alumina, zirconia, silicon carbide, or combinations thereof. Diluent material 14 may be of similar density than that of catalyst structures 13, but not necessarily. In some preferred embodiments, diluent material 14 comprises the same or similar material as used for supporting catalyst structures 13. As a non-limiting example, alpha-alumina particles can be used as diluent material 14, and catalyst structures 13 comprise particles of alumina. However, it is not necessary that diluent material 14 and catalyst structures 13 comprise the same or similar refractory oxide. As a non-limiting example, silicon carbide particles can be used as diluent material 14, and catalyst structures 13 comprise particles of alumina or zirconia. One skilled in the art can determine the length of combustion catalyst bed 12 based on the selection of diluent material 14, catalyst particles 13, and their corresponding weight ratio to be used in combustion catalyst bed 12.

A heating zone 16 within alkene production zone 15 is in thermal contact with combustion zone 10, and a dividing element 18 between heating zone 16 and combustion catalyst bed 12 does not allow permeation of gaseous components to and from heating zone 16 and combustion catalyst bed 12. Dividing element 18 also defines the zone of thermal contact. Alkane feed 60 flows through heating zone 16 in the same direction as the gas phase in combustion catalyst bed 12. Such thermal contact in heating zone 16 allows alkane feed 60 to absorb some of the heat generated by the combustion of combustion feed 50, so as to initiate the oxidative reaction in alkene production zone 15 with such absorbed heat. Without limitation, the time period for thermal contact between alkane feed 60 and combustion catalyst bed 12 depends on the length of combustion catalyst bed 12 and/or the superficial velocity of alkane feed 60 along dividing element 18 in heating zone 16. The longer the length and/or the lower the velocity of superficial velocity of alkane feed 60, the higher the time of thermal contact. The size of combustion catalyst bed 12 in longitudinal and radial directions will also influence the surface area of dividing element 18 available for heat exchange, and therefore the heat exchange efficiency. Alkane feed 60 should not be in fluid contact in heating zone 16 along combustion catalyst bed 12, so as to prevent reaction between alkane feed 60 and the content of combustion catalyst bed 12. Thus, dividing element 18 between heating zone 16 and combustion catalyst bed 12, which defines the area of thermal contact between alkane feed 60 and combustion catalyst bed 12, is preferably not permeable to gaseous components of alkane feed 60 and gases in combustion catalyst bed 12. However, dividing element 18 should have a sufficient thermal conductivity so as to transfer a substantial amount of heat from combustion catalyst bed 12 to heating zone 16 such that alkane feed 60 passing alongside combustion catalyst bed 12 in alkene production zone 15 absorbs at least a portion of the heat. The addition of diluent material 14 in combustion catalyst bed 12 is not only expected to increase the combustion zone volume (i.e. length) of the elongated combustion catalyst bed 12 bat is also expected, like the addition of a diluent gas in combustion feed 50, to control the rate in which the heat of combustion in combustion zone 10 is generated.

The following describes an exemplary application of the present invention as illustrated in FIG. 2. Combustion feed 50 is fed to combustion zone 10 and contacted with catalyst structures 13 in combustion catalyst bed 12. Combustion feed 50 is a gas comprising steam and/or an oxygen-containing gas, preferably an oxygen-containing gas; a fuel; and optionally a diluent gas. The fuel comprises hydrogen, carbon monoxide, C1–C4 alkanes such as methane, C1–C4 alkenes, naphtha, natural gas, syngas, or mixtures thereof, preferably methane. Without limitation, examples of suitable oxygen-containing gases include substantially pure oxygen ($O_2$); air; $O_2$-enriched air; $O_2$ diluted with an inert gas such as nitrogen; any recycle stream or effluent stream from another unit, which may comprise a significant $O_2$ content, and which may have been sent through a separation unit in order to concentrate its $O_2$ content. In alternative embodiments, the fuel for combustion may comprises any gas or liquid hydrocarbon, hydrogen, carbon monoxide, carbon dioxide, natural gas, or combinations thereof. Diluent gas can comprise any gas that is inert (non-reactive) under combustion conditions, i.e., would not significantly impact the combustion reaction (does not act as a poison). Without limitation, examples of diluent gas include nitrogen, argon, and helium, preferably nitrogen. Preferably, a diluent gas is present in combustion feed 50 in an amount between about 1 to about 50% by volume, and more preferably no diluent gas is present in combustion feed 50. Preferably, combustion feed 50 is pre-heated in preheater 40 before being fed to combustion zone 10. Combustion catalyst bed 12 is preferably a diluted catalyst bed as described above. Combustion catalyst bed 12 and/or combustion feed 50 can be diluted with diluent material 14 or a diluent gas, respectively, but preferably only combustion catalyst bed 12 is diluted. Preferably, combustion feed 50 is pre-heated to temperatures up to about 600° C.; more preferably up to about 500° C., and still more preferably from about 200° C. to about 400° C. The pre-heated combustion feed 50 is fed to combustion zone 10 in which the fuel is combusted or partially combusted. Combustion zone 10 can operate at any conditions sufficient for the combustion or partial combustion of the fuel. For instance, combustion zone 10 preferably operates at pressures of about 100 psig or more, more preferably at about 200 psig or more, and still more preferably between about 400 psig and about 550 psig. The gas hourly space velocity (GHSV) of combustion zone 10 is preferably from about 10,000 $hr^{-1}$ to about 1,000,000 $hr^{-1}$, and more preferably from about 10,000 $hr^{-1}$ to about 100,000 $hr^{-1}$. In addition, the gas phase temperature in combustion zone 10 should be from about 200° C. to about 1,600° C., preferably from about 200° C. to about 1,200° C., more preferably from about 300° C. to about 650° C. Combustion zone effluent 55 exits combustion zone 50 at temperatures from about 200° C. to about 1,000° C., more preferably at temperatures from about 300° C. to about 900° C., and still more preferably at temperatures from about 300° C. to about 700° C.

Combustion zone effluent 55 contains heat produced in combustion zone 10 and also comprises syngas, water, carbon dioxide, unconverted fuel such as methane, hydrogen, carbon monoxide, or mixtures thereof Combustion zone effluent 55 may or may not contain oxygen.

In some embodiments, a substantial portion of the oxygen in combustion feed 50 is consumed in combustion zone 10 such that combustion zone effluent 55 comprises preferably less than 1,000 ppm oxygen, more preferably less than 500 ppm oxygen, and still more preferably less than 100 ppm oxygen. In some embodiments, combustion zone effluent 55 comprises substantially no oxygen. The complete utilization of oxygen comprised in combustion feed 50 in combustion zone 10 is due to the selection of an oxygen-to-fuel ratio in combustion feed 50 such that the fuel is in stoichiometric excess. The fuel comprises a molar $O_2$:C ratio less than 1:2. When the fuel comprises CO, combustion feed 50 may have an $O_2$:C molar ratio less than 1:2, preferably between about 8:1 and about 12:1. When the fuel comprises methane, combustion feed 50 may have a $CH_4$:$O_2$ molar ratio greater than 1:2, preferably between about 15:1 and about 20:1. When the fuel comprises hydrogen, combustion feed 50 may have a $H_2$:$O_2$ molar ratio greater than 2:1, preferably between about 5:1 and about 10:1. In this embodiment, it may be desirable that alkane feed 60 also comprises an oxygen-containing gas. While alkane feed 60 comprising both an alkane and oxygen is heated through heating zone 16, it is expected that at least a portion of the alkane may be converted to an alkene by a non-catalytic reaction in heating zone 16, especially if the heat transfer from combustion zone 10 to heating zone 16 is sufficient for alkane feed 60 to reach a temperature sufficient to initiate such reaction between the alkane and oxygen before the heated alkane feed 60 exits heating zone 16.

In other embodiments, a substantial portion of the oxygen in combustion feed 50 is not consumed in combustion zone 10 with combustion zone effluent 55, such that combustion zone effluent 55 comprises more than 1,000 ppm oxygen. The incomplete utilization of oxygen comprised in combustion feed 50 in combustion zone 10 is typically due to the selection of an oxygen-to-fuel ratio in combustion feed 50 such that the oxygen is in stoichiometric excess. When the fuel comprises CO, combustion feed 50 may have a CO:$O_2$ molar ratio less than 2:1. When the fuel comprises methane, combustion feed 50 may have a $CH_4$:$O_2$ molar ratio less than 1:2. When the fuel comprises hydrogen, combustion feed 50 may have a $H_2:O_2$ molar ratio less than 2:1.

Alkane feed 60 is fed to alkene production zone 15. The flow rate of alkane feed 60 to reactor 5 can be any suitable rate. Preferably, alkane feed 60 is fed to reactor 5 at a molar ratio of alkane feed 60 to combustion feed 50 from 5:1 to 20:1, more preferably from 8:1 to 15:1, and most preferably at about 10:1. Alkane feed 60 is a gas comprising at least one alkane. Alkane feed 60 can comprise any alkanes, preferably ethane. In alternative embodiments, alkane feed 60 may also comprise an oxygen-containing gas, or steam, or both. Without limitation, examples of suitable oxygen-containing gases include substantially pure oxygen ($O_2$); air; $O_2$-enriched air; $O_2$ diluted with an unreactive gas such as nitrogen; any recycle stream or effluent stream from another unit, which may comprise a significant $O_2$ content, and which may have been sent through a separation unit in order to increase its $O_2$ content. The alkane to oxygen molar ratio can be any suitable ratio for use in reactor 5, preferably from about 1.6:1 to about 10:1, more preferably from about 2:1 to about 4:1. Alkane feed 60 can be fed at ambient temperature to alkene production zone 15 or can be pre-heated in preheater 45 before being fed to alkene production zone 15. In preheater 45, alkane feed 60 is pre-heated to temperatures from about 100° C. to about 600° C., more preferably from about 200° C. to about 400° C. Preferably, pre-heating alkane feed 60 allows for less combustion feed 50 to be fed to reactor 5.

It is to be understood that the reactor conditions and other parameters can be controlled to obtain any desired alkane conversion and alkene selectivity in alkene production zone 15 with the absorption by alkane feed 60 of the heat generated in combustion zone 10 driving the dehydrogenation reaction. For instance, alkene production zone 15 preferably operates at pressures of about 2 psig or more, more preferably at about 45 psig or more, still more preferably at about 90 psig or more, and yet still more preferably between 100 psig and about 500 psig. In some embodiments, the pressure may be between about 100 kPa (14.7 psia) to about 1,030 kPa (150 psia). In other embodiments, the pressure can be between about 100 kPa (about 14.5 psia) to about 500 kPa (about 72.5 psia). The gas hourly space velocity (GHSV) of alkene production zone 15 is preferably from about 20,000 $hr^{-1}$ to about 10,000,000 $hr^{-1}$, and more preferably from about 50,000 $hr^{-1}$ to about 4,000,000 $hr^{-1}$. In addition, the reaction temperature in alkene production zone 15 is preferably from about 600° C. to about 1,200° C., more preferably from about 600° C. to about 1000° C. The preferable alkene is ethylene. Preferred alkane conversion is at least about 40 percent, and the alkene selectivity is at least about 30 percent. More preferably, the alkane conversion is at least about 50 percent, and the alkene selectivity is at least about 50 percent. Still more preferably, the alkane conversion is at least about 60 percent, and the alkene selectivity is at least about 55 percent. Most preferably, the alkane conversion is at least about 65 percent, and the alkene selectivity is at least about 60 percent.

The alkene production effluent 80 exiting heating zone 16 comprises the heated alkane feed 60 in which at least a portion of the alkanes in alkane feed 60 may have been converted to alkenes. In some embodiments when a noncatalytic reaction in heating zone 16 takes place and generates an alkene from an alkane, alkene production effluent 80 may be mixed with combustion zone effluent 55 to produce mixed product stream 85, which exits reactor 5 as reactor effluent 65. In alternative embodiments (not illustrated), alkene production effluent 80 exits reactor 5 without being mixed with combustion zone effluent 55. Such alternative embodiments are desirable if the catalytic alkene production reaction has a desirable alkane conversion, alkene selectivity, and/or alkene yield.

In other alternative embodiments (not illustrated), when a noncatalytic alkene production reaction in heating zone 16 does not take place (no $O_2$ presence in alkane feed 60) or generates insufficient amounts of an alkene from an alkane (with $O_2$ presence in alkane feed 60), alkene production catalyst bed is used. Mixed product stream 85 can be fed to alkene production catalyst bed for a second dehydrogenation reaction that further converts alkanes to alkenes, preferably ethylene. In such an alternative embodiment, the preferable alkane conversion in alkene production catalyst bed is at least about 30 percent, and the alkene selectivity is at least about 40 percent. More preferably, the alkane conversion is at least about 40 percent, and the alkene selectivity is at least about 50 percent. Still more preferably, the alkane conversion is at least about 50 percent, and the alkene selectivity is at least about 60 percent. Alkene production catalyst bed can operate at any conditions sufficient to initiate the oxidative dehydrogenation reaction to produce alkenes. For instance, alkene production catalyst bed preferably operates at pressures, gas hourly space velocity (GHSV), and temperature as described earlier for FIG. 2. It is to be understood that the alkene production catalyst bed of this alternative embodiment is similar to alkene production catalyst bed 17 of previous embodiments.

In additional alternative embodiments wherein mixed product stream 85 is fed to alkene production catalyst bed, superheated oxygen, carbon dioxide, and/or steam can result in diluting alkane feed to the alkene production zone, in addition to or in place of using a diluent gas (such as nitrogen, argon, helium) in combustion feed 50. In such alternative embodiments, oxygen is in excess in combustion feed 50 over that required for complete combustion of all the fuel in combustion zone 10. Thus, the excess oxygen (superheated by passing through combustion zone 10) serves as a diluent gas and provides oxygen for the reaction which takes place in alkene production zone 15. Such superheated oxygen, carbon dioxide, and/or steam are generated by an excess of oxygen-containing gas and/or steam in combustion feed 50. Such an excess preferably occurs without incomplete combustion in combustion zone 10. To have an excess of oxygen containing gas and/or steam in combustion feed 50, oxygen-containing gas and/or steam are present in combustion feed 50 in a molar ratio of atomic oxygen-to-carbon (O:C) greater than 2:1 when the combustion feed comprises an alkane as the fuel such as methane; and particularly for oxygen-containing gas, a molar ratio of dioxygen-to-carbon ($O_2$:C) greater than 2:1 The molar ratio of atomic oxygen-to-carbon (O:C) present in combustion feed 50 should be greater than 1:2 when the combustion feed comprises CO as the fuel. Such superheated oxygen, carbon dioxide, and/or steam comprise temperatures from about 500° C. to about 2,000° C., and preferably from about 1,000° C. to about 2,000° C. upon exiting combustion zone 10 in combustion zone effluent 55.

In further alternative embodiments (not illustrated), alkene production effluent 80 is not combined with combustion zone effluent 55. Instead, alkene production effluent 80 and combustion zone effluent 55 exit reactor 5 as separate effluents.

Figure 3:
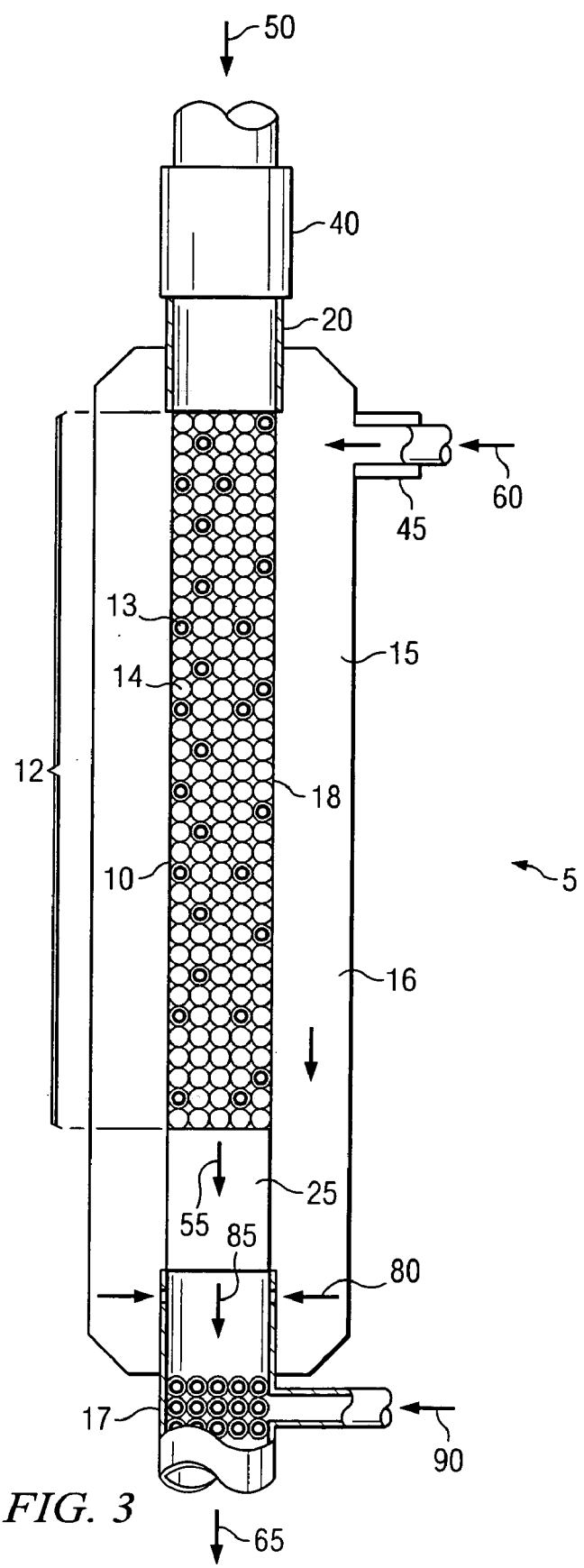
FIG. 3 illustrates a two-zone alkene production reactor having a first reaction zone comprising a diluted catalytic bed, and a second reaction zone comprising a heating zone, an optional catalyst bed and a supplemental oxygen stream.

FIG. 3 illustrates an embodiment of the invention that is similar to FIG. 2 but has a supplemental oxygen stream 90 that is fed downstream of alkene production zone 15. Alkene production catalyst bed 17 is optional. Alternatively, in lieu of the optional alkene production catalyst bed 17, a bed comprising a refractory material (such as an inorganic oxide like alumina, zirconia, and the like) that is substantially free of catalytic metal may be placed downstream of combustion zone 10. Supplemental oxygen stream 90 comprises an oxygen-containing gas. Without limitation, examples of suitable oxygen-containing gases include substantially pure oxygen ($O_2$); air; $O_2$-enriched air; $O_2$ diluted with an inert gas such as nitrogen; any recycle stream or effluent stream from another unit, which may comprise a significant $O_2$ content, and which may have been sent through a separation unit in order to concentrate its $O_2$ content.

The following describes an exemplary application of the present invention as embodied and illustrated in FIG. 3, which comprises substantially all of the elements of the above discussed embodiments as illustrated in FIG. 2 and alternative embodiments thereof, with the additional elements discussed below. After alkene production effluent 80 exits heating zone 16 of alkene production zone 15, it is preferably mixed with combustion zone effluent 55 to produce mixed product stream 85. Supplemental oxygen stream 90 can be fed to reactor 5 and mixed with mixed product stream 85, which exits reactor 5 as reactor effluent 65. Supplemental oxygen stream 90 is fed to reactor 5 in any amounts suitable to consume at least a portion of any hydrogen in mixed product stream 85 and form steam. Combustion of the hydrogen with the oxygen can produce heat. Such production of heat can further the oxidative dehydrogenation reaction and produce alkenes from alkanes in mixed product stream 85. Combustion zone effluent 55 may or may not contain oxygen depending on the oxygen-to-carbon ratio used in combustion feed 50. In a preferred embodiment of FIG. 3, combustion zone effluent 55 may contain below 1,000 ppm of oxygen; more preferably less than 500 ppm oxygen; still more preferably less than 100 ppm oxygen. In other embodiments, combustion zone effluent 55 is substantially free of oxygen. In additional embodiments, combustion zone effluent 55 comprises more than 1,000 ppm oxygen. In alternative embodiments, mixed product stream 85 is fed to alkene production catalyst bed 17 for further production of alkenes, preferably ethylene. In such an alternative embodiment, supplemental oxygen stream 90 can be fed directly to alkene production catalyst bed 17 and/or can be mixed with mixed product stream 85, which is then fed to alkene production catalyst bed 17. In further alternative embodiments (not illustrated), supplemental oxygen stream 90 can be fed to reactor effluent 65.

In further alternative embodiments (not illustrated), alkene production effluent 80 is not combined with combustion zone effluent 55. Instead, alkene production effluent 80 and combustion zone effluent 55 exit reactor 5 as separate effluents. In such alternative embodiments, supplemental oxygen stream 90 can be mixed with alkene production effluent 80 to further the dehydrogenation reaction.

To further illustrate various illustrative embodiments of the present invention, the following examples are provided.

EXAMPLES 1–3

The experiments were performed in a ½ inch quartz reactor comprising a combustion zone comprising a ceramic shield and an alkene production zone. All experiments were conducted at approximately atmospheric pressure. Three Examples were performed to demonstrate the use of the heat from the combustion of carbon monoxide with $O_2$ to initiate an alkene production reaction with ethane, $O_2$ and optionally $H_2$. The combustion zone feed, also called main feed, comprised CO, $O_2$ and optionally $H_2$, which were separately supplied via gas cylinders. The feed to the alkene production zone, called side feed, comprised ethane, $O_2$, and optionally $H_2$ and was not heated. The individual components of the side feed were mixed in a static mixer outside the reactor. The individual components of the main feed were mixed in a static mixer outside the reactor and heated before entering the combustion catalyst bed. The inlet temperature of the main feed, directly above the ceramic shield, was set at 400° C. The combustion zone in all three Examples included a diluted bed comprising particles of alpha-alumina (used as a diluent material) and particles of a combustion catalyst supported on the same alpha-alumina material with a weight ratio of diluent material-to-catalyst of 3:1. The alpha alumina particles were about 1 mm in size. The catalyst bed in combustion zone had a bed depth of about 0.625 inch. The combustion catalyst used in all three Examples was composed of a 1.0% Pt supported on alpha $Al_2O_3$. An alkene production catalyst used solely in Example 1 had the following composition: 0.1 g Pd-0.4 g Cu-2.4 g Mn on 100 g of zirconia Example 2 employed a bed containing an alpha-alumina material in the alkene production zone, which did not contain any catalytic metal. The alkene production zone in Example 3 did not contain a catalyst or an inorganic oxide material. The experimental setup can be illustrated by FIG. 2, except that the alkene production zone contained an alkene production bed with an alkane production catalyst and with an alpha-alumina material for Examples 1 and 2, respectively.

Three examples were conducted with each having multiple reaction conditions. The philosophy behind each example was the same. Experiments were conducted with 400° C. preheat in the main feed and no preheat for the side feed.

A baseline run (runs 1A; 1B; 1C for Examples 1–3, respectively) was first obtained during which CO and $O_2$ were run through the combustion catalyst in the top bed. $N_2$ was added as a diluent gas to keep the linear velocity above the flame speed. Ethane and $O_2$ were co-fed in the side feed (without $H_2$ addition) and mixed with the combustion products and thereafter run through the alkene production zone.

Example 1

In Example 1, the second run condition (run 2A) involved $H_2$ addition to the side feed, and the third run condition (run 3A) doubled the $H_2$ flow, since co-fed $H_2$ has been shown to increase ethylene selectivity. The fourth run condition (run 4A) involved maintaining the $H_2$ flow in the side feed while increasing the ethane to $O_2$ ratio in an effort to further increase ethylene selectivity.

The results of Example 1 are shown in Table 1. Each mole % in the table represents an average of 2–4 gas chromatograph analyses. The transition from condition 1A to condition 2A involved the addition of 0.25 liters per minute of $H_2$. Ethane conversion dropped upon the addition of $H_2$ while ethylene selectively improved. The transition from condition 2A to condition 3A involved the addition of another 0.25 liters per minute of $H_2$. Again, ethane conversion decreased while ethylene selectivity increased. Changing from condition 3A to condition 4A involved increasing the ethane to oxygen ratio in the side feed. This transition also caused an increase in ethylene selectivity at the expense of ethane conversion. The preheat temperature of the main feed (Preheat Temp.), the flow rates in standard cubic centimeters per minute (sccm) of the hydrogen flow in side feed (Hydrogen-SF), the ethane flow in side feed (Ethane-SF), the CO flow in main feed (Carbon Monoxide-MF), the oxygen flow in side feed (Oxygen-SF), the oxygen flow in main feed (Oxygen-MF), and the nitrogen flow in main feed (Nitrogen-MF) for each condition 1A–4A are listed in Table 2.

TABLE 1

Results for Example 1

|  | Run 1A (Mole %) | Run 2A (Mole %) | Run 3A (Mole %) | Run 4A (Mole %) |
|---|---|---|---|---|
| Ethane Conversion | 71.6 | 70.9 | 70.1 | 60.7 |
| Ethylene Selectivity | 64.2 | 64.9 | 65.1 | 66.3 |

TABLE 1-continued

Results for Example 1

|  | Run 1A (Mole %) | Run 2A (Mole %) | Run 3A (Mole %) | Run 4A (Mole %) |
|---|---|---|---|---|
| Ethylene Yield | 46.0 | 46.0 | 45.6 | 40.2 |
| Methane Selectivity | 20.6 | 21.1 | 21.9 | 17.0 |
| Acetylene Selectivity | 0.3 | 0.3 | 0.3 | 0.1 |
| Propylene Selectivity | 1.5 | 1.3 | 1.3 | 1.3 |

TABLE 2

Run Conditions for Example 1

| Run Condition | Preheat Temp. (° C.) | Hydrogen (SF) (sccm) | Ethane (SF) (sccm) | Carbon Monoxide (MF) (sccm) | Oxygen (SF) (sccm) | Oxygen (MF) (sccm) | Nitrogen (MF) (sccm) |
|---|---|---|---|---|---|---|---|
| 1A | 400 | 0 | 1660 | 900 | 638 | 250 | 750 |
| 2A | 400 | 250 | 1660 | 500 | 638 | 250 | 750 |
| 3A | 400 | 500 | 1660 | 500 | 638 | 250 | 750 |
| 3A | 400 | 500 | 1730 | 500 | 577 | 250 | 750 |

Example 2

For Example 2, an alpha $Al_2O_3$ material was used as the second bed rather than the alkene production catalyst used in Example 1. Example 2 had five conditions 1B–5B. Conditions 1B–4B were the same as conditions 1A–4A of Example 1, and condition 5B employed an excess of oxygen in the main feed (see Table 3 for conditions). Example 2 was performed to introduce heated $O_2$ to the ethane side feed to find out if the heated $O_2$ would be more reactive. The same trends for ethane conversion and ethylene selectivity from Example 1 were seen in Example 2. Ethylene selectivity constantly increased from conditions 1B to 4B while ethane conversion constantly decreased. For condition 5B, ethane conversion increased with a slight fall in ethylene selectivity, indicating that the heated $O_2$ is very reactive but responsible for some incremental combustion of ethane. The results of Example 2 are shown in Table 4.

TABLE 3

Run Conditions for Example 2

| Run Condition | Preheat (° C.) | Hydrogen (SF) (sccm) | Ethane (SF) (sccm) | Carbon Monoxide (MF) (sccm) | Oxygen (SF) (sccm) | Oxygen (MF) (sccm) | Nitrogen (MF) (sccm) |
|---|---|---|---|---|---|---|---|
| 1B | 400 | 0 | 1660 | 500 | 638 | 250 | 750 |
| 2B | 400 | 250 | 1660 | 500 | 638 | 250 | 750 |
| 3B | 400 | 500 | 1660 | 500 | 638 | 250 | 750 |
| 4B | 400 | 500 | 1730 | 500 | 577 | 250 | 750 |
| 5B | 400 | 500 | 1730 | 500 | 577 | 300 | 750 |

TABLE 4

Results for Example 2

|  | Run 1B (Mole %) | Run 2B (Mole %) | Run 3B (Mole %) | Run 4B (Mole %) | Run 5B (Mole % |
|---|---|---|---|---|---|
| Ethane Conversion | 71.3 | 70.6 | 68.8 | 50.3 | 54.9 |
| Ethylene Selectivity | 65.0 | 65.2 | 66.1 | 67.7 | 66.7 |
| Ethylene Yield | 46.3 | 46.0 | 45.5 | 34.0 | 36.6 |
| Methane Selectivity | 25.3 | 27.6 | 28.4 | 17.4 | 19.0 |
| Acetylene Selectivity | 0.5 | 0.4 | 0.4 | 0.0 | 0.4 |
| Propylene Selectivity | 1.9 | 1.9 | 1.9 | 1.3 | 1.3 |

Example 3

For Example 3, an empty tube was used in the alkene production zone rather than a second bed. Examples 3 had six conditions (1C–6C). Conditions 1C–4C were the same as conditions 1A–4A of Example 1. Two conditions 5C and 6C were added to Example 3, which used less CO and $O_2$ in the main feed. Condition 5C had higher than normal $N_2$ dilution in the main (combustion) feed, and condition 6C had lower than normal $N_2$ dilution in the main feed (see Table 5). The results of Example 3 are shown in Table 6. Again, the same trend is recognized, where ethylene selectivity increases from conditions 1C to 4C, with very poor results for Conditions 5C and 6C, most likely resulting from insufficient heat supplied to continue the conversion of ethane to ethylene. (Condition 6C is not shown in Table 6, but performance was not as good as for condition 5C).

TABLE 5

Run Conditions for Example 3

| Run Condition | Preheat (° C.) | Hydrogen (SF) (sccm) | Ethane (SF) (sccm) | Carbon Monoxide (MF) (sccm) | Oxygen (SF) (sccm) | Oxygen (MF) (sccm) | Nitrogen (MF) (sccm) |
|---|---|---|---|---|---|---|---|
| 1C | 400 | 0 | 1660 | 500 | 638 | 250 | 750 |
| 2C | 400 | 250 | 1660 | 500 | 638 | 250 | 750 |
| 3C | 400 | 500 | 1660 | 500 | 638 | 250 | 750 |
| 4C | 400 | 500 | 1730 | 500 | 577 | 250 | 750 |
| 5C | 400 | 500 | 1730 | 300 | 577 | 150 | 1050 |
| 6C | 400 | 500 | 1730 | 300 | 577 | 150 | 450 |

TABLE 6

Results for Example 3

|  | Run 1C (Mole %) | Run 2C (Mole %) | Run 3C (Mole %) | Run 4C (Mole %) | Run 5C (Mole % |
|---|---|---|---|---|---|
| Ethane Conversion | 70.5 | 70.4 | 69.6 | 60.4 | 2.3 |
| Ethylene Selectivity | 64.0 | 64.4 | 64.6 | 65.6 | 29.7 |
| Ethylene Yield | 45.2 | 45.4 | 45.0 | 39.7 | 1.2 |
| Methane Selectivity | 19.9 | 21.5 | 22.1 | 20.7 | 2.7 |
| Acetylene Selectivity | 0.3 | 0.3 | 0.3 | 0.1 | 0.0 |
| Propylene Selectivity | 1.5 | 1.4 | 1.3 | 1.5 | 0.0 |

The results of the three Examples provide a number of conclusions. Comparing the first four identical run conditions for the three Examples shows that there was very little difference between reactions occurring over an alkene production catalyst and reactions occurring only in the gas phase without a catalyst. The best performance, measured by ethylene selectivity, came from the use of an alpha-alumina bed in the alkene production zone. This was likely due to better mixing of the reactants and better heat containment that the alpha-alumina bed (in Example 2) provided over the empty tube (in Example 3). This indicates that there may be a substantial homogenous contribution to the alkane-to-alkene oxidative reaction and that the alkene production catalyst may not be as effective as one would have expected.

One reason that the alkene production catalyst may have been ineffective may have been the distance between the bottom (alkene production) bed and the remixing point of the reactants. In all experimental runs, the $O_2$ was completely consumed. It is likely that the $O_2$ was consumed in the spacing between the top (combustion) and bottom (alkene production) beds, and since the alkane-to-alkene oxidative reaction rate rapidly declines after $O_2$ is consumed, the catalyst could have been ineffective because of a lack of $O_2$ rather than a lack of activity.

Overall, there was very little difference in the performance with and without the presence of an alkene production catalyst. The ethylene selectivity in the presence of the alpha-alumina bed was actually higher than in the presence of the alkene production catalyst, indicating that the alkene production catalyst may be converting ethane into undesirable co-products. However, the conversion was consistently higher in the presence of the alkene production catalyst. This was expected, since the alkene production catalyst in Example 1 provided an additional source of combustion (with the help of the precious metal, Pd) that the alphaalumina bed and the empty tube configurations did not have in Examples 2 and 3, respectively.

Although the present invention and its advantages have been described in detail, it should be understood that various changes, substitutions and alterations may be made herein without departing from the spirit and scope of the invention as defined by the appended claims.

What is claimed is:

1. A process for the production of alkenes from alkanes, comprising:
   (A) feeding a first zone feed to a first reaction zone having a combustion catalyst, wherein the first zone feed comprises an oxygen-containing gas and a fuel;
   (B) contacting the first zone feed with the combustion catalyst under conditions sufficient to combust at least a portion of the fuel so as to form a first reaction zone effluent having less than about 1,000 ppm oxygen;
   (C) feeding the first reaction zone effluent to a second reaction zone;
   (D) introducing an oxygen-containing feed and an alkane feed to the second reaction zone; and
   (E) reacting at least a portion of the alkane feed with oxygen in the second reaction zone at conditions sufficient to form an alkene product.

2. The process of claim 1, wherein the fuel comprises hydrogen, carbon monoxide, C1–C4 alkanes, C1–C4 alkenes, naphtha, natural gas, syngas, or mixtures thereof.

3. The process of claim 2, wherein the first zone feed has a molar $O_2$:C ratio less than 2:1.

4. The process of claim 1, wherein the fuel comprises carbon monoxide.

5. The process of claim 4, wherein the first zone feed has a molar $O_2$:C ratio less than 1:2.

6. The process of claim 1, wherein step (A) further comprises preheating the first zone feed prior to feeding the first zone feed to the first reaction zone.

7. The process of claim 1, wherein the conditions sufficient of step (B) include temperatures of from about 200° C. to about 1,000° C.

8. The process of claim 1, wherein the combustion catalyst comprises platinum, palladium, rhodium, ruthenium, iridium, osmium, chromium, or combinations thereof.

9. The process of claim 1, wherein the combustion catalyst comprises platinum, palladium, chromium, or combinations thereof.

10. The process of claim 1, wherein the first reaction zone comprises a diluted catalytic bed comprising the combustion catalyst and a diluent material.

11. The process of claim 10, wherein the diluent material comprises a refractory oxide.

12. The process of claim 1, wherein the first reaction zone effluent comprises less than 100 ppm oxygen.

13. The process of claim 1, wherein the second reaction zone comprises an inorganic oxide.

14. The process of claim 1, wherein the second reaction zone excludes a catalyst.

15. The process of claim 1, wherein the second reaction zone includes a catalyst comprising a metal from the group consisting of Groups 2, 4–7, 11–15 metals of the Periodic Table of the Elements, scandium, yttrium, actnium, iron, cobalt, nickel, oxides of any such metals, and combinations thereof.

16. The process of claim 1, wherein the alkane feed and the oxygen-containing feed are mixed prior to being introduced in step (D) to the second reaction zone.

17. The process of claim 1, wherein the alkane feed comprises ethane.

18. The process of claim 1, wherein the alkane feed further comprises oxygen.

19. The process of claim 18, wherein the alkane feed comprises an alkane to oxygen molar ratio of from about 1.6:1 to about 10:1.

20. The process of claim 1, wherein the conditions sufficient of step (E) include temperatures from about 600° C. to about 1,200° C.

21. The process of claim 1, wherein the process comprises an alkane conversion of at least about 60 percent, and an alkene selectivity of at least about 50 percent.

22. The process of claim 1, wherein the second reaction zone comprises a heating zone in thermal contact with the first reaction zone, and wherein step (D) further comprises heating the alkane feed through the heating zone by heat transfer from the first reaction zone to the heating zone.

23. The process of claim 22, wherein the alkane feed and the oxygen-containing feed are introduced separately, and the oxygen-containing feed is introduced to the second reaction zone without passing through the heating zone.

24. A process for the production of alkenes from alkanes, comprising:
   (A) feeding a first zone feed to a first reaction zone having a combustion catalyst, wherein the first zone feed comprises an oxygen-containing gas and a fuel;
   (B) contacting the first zone feed with the combustion catalyst under conditions sufficient to combust at least a portion of the fuel so as to produce heat and a combustion zone effluent;
   (C) feeding an alkane feed to a second reaction zone comprising a heating zone, wherein the heating zone is in thermal contact with the first reaction zone through a dividing element that allows at least a fraction of the heat produced in the first reaction zone to be transferred to the heating zone, and wherein the dividing element does not allow permeation of gaseous components to and from the heating zone and the first reaction zone, and further wherein the alkane feed passes through the heating zone and absorbs a sufficient amount of the heat produced in the first reaction zone to initiate the conversion of at least one alkane to an alkene in the second reaction zone; and
   (D) converting at least a portion of the alkane feed so as to form an alkene product.

25. The process of claim 24, wherein the fuel comprises hydrogen, carbon monoxide, C1–C4 alkanes, C1–C4 alkenes, naphtha, natural gas, syngas, or mixtures thereof.

26. The process of claim 24, wherein the alkane feed comprises ethane, and wherein the alkene product comprises ethylene.

27. The process of claim 24, wherein the alkane feed further comprises an oxygen-containing gas.

28. The process of claim 27, wherein the alkane feed comprises an alkane to oxygen molar ratio of from about 1.6:1 to about 10:1.

29. A process for the production of alkenes from alkanes, comprising:
   (A) feeding a first zone feed to a first reaction zone having a combustion catalyst, wherein the first zone feed comprises an oxygen-containing gas and a fuel;
   (B) contacting the first zone feed with the combustion catalyst under conditions sufficient to combust at least a portion of the fuel so as to form a first reaction zone effluent;
   (C) providing an alkene production zone comprising a heating zone in thermal contact with the first reaction zone through a dividing element that allows at least a fraction of the heat produced in the first reaction zone to be transferred to the heating zone and wherein the dividing element does not allow permeation of gaseous components to and from the heating zone and the first reaction zone, and further wherein the alkene production zone excludes a catalyst;

(D) passing the first reaction zone effluent to the alkene production zone;

(E) introducing an alkane feed to the alkene production zone;

(F) heating the alkane feed through the heating zone of the alkene production zone by heat transfer from the first reaction zone to the heating zone; and (G) reacting at least a portion of the alkane feed with oxygen in the alkene production zone at conditions sufficient to form an alkene product.

30. The process of claim 29, wherein the fuel comprises hydrogen, carbon monoxide, C1–C4 alkanes, C1–C4 alkenes, naphtha, natural gas, syngas, or mixtures thereof.

31. The process of claim 30, wherein the first zone feed has a molar $O_2$:C ratio less than 2:1.

32. The process of claim 29, wherein the fuel comprises carbon monoxide.

33. The process of claim 32, wherein the first zone feed has a molar $O_2$:C ratio less than 1:2.

34. The process of claim 29, wherein step (A) further comprises preheating the first zone feed prior to feeding the first zone feed to the first reaction zone.

35. The process of claim 29, wherein the conditions sufficient of step (B) include temperatures of from about 200° C. to about 1,000° C.

36. The process of claim 29, wherein the combustion catalyst comprises platinum, palladium, chromium, or combinations thereof.

37. The process of claim 29, wherein the first reaction zone comprises a diluted catalytic bed comprising the combustion catalyst and a diluent material.

38. The process of claim 37, wherein the diluent material comprises a refractory oxide.

39. The process of claim 37, wherein the diluted catalytic bed comprises a diluent material-to-catalyst weight ratio between about 1:2 and about 10:1.

40. The process of claim 29, wherein the alkene production zone comprises an inorganic oxide.

41. The process of claim 29, wherein the alkane feed comprises ethane, and the alkene product comprises ethylene.

42. The process of claim 29, wherein the alkane feed further comprises oxygen.

43. The process of claim 42, wherein the alkane feed comprises an alkane to oxygen molar ratio of from about 1.6:1 to about 10:1.

44. The process of claim 29, wherein the conditions sufficient of step (G) include temperatures from about 600° C. to about 1,200° C.

45. The process of claim 29, wherein the process comprises an alkane conversion of at least about 60 percent, and an alkene selectivity of at least about 50 percent.

46. The process of claim 29, further comprising introducing a supplemental oxygen feed to the alkene production zone without passing it through the heating zone.

47. The process of claim 29, wherein the first reaction zone effluent contains at least 1000 ppm oxygen.

48. The process of claim 24, wherein the second reaction zone includes a catalyst.

49. The process of claim 24, wherein the combustion zone effluent comprises less than about 1,000 ppm oxygen.

50. The process of claim 49, wherein the alkane feed further comprises an oxygen-containing gas.

51. The process of claim 24, wherein the alkane feed flows through the heating zone in the same direction as the gaseous components in the first reaction zone.

52. The process of claim 24, wherein the alkane feed is fed at ambient temperature to the second reaction zone.

53. The process of claim 24, wherein the alkene product exits the heating zone of the second reaction zone and mixes with the combustion zone effluent to form a mixed product stream.

54. The process of claim 53, wherein the mixed product stream is fed to an alkene production catalyst bed.

55. The process of claim 54, wherein a supplemental oxygen stream is further fed to the alkene production catalyst bed.

56. A process for the production of alkenes from alkanes, comprising:

(A) feeding a first zone feed to a first reaction zone having a syngas catalyst, wherein the first zone feed comprises an oxygen-containing gas and a fuel;

(B) contacting the first zone feed with the syngas catalyst under conditions sufficient to react at least a portion of the fuel with oxygen so as to produce heat and a first zone effluent comprising carbon monoxide, optionally carbon dioxide, and hydrogen;

(C) feeding an alkane feed to a second reaction zone comprising a heating zone, wherein the heating zone is in thermal contact with the first reaction zone through a dividing element that allows at least a fraction of the heat produced in the first reaction zone to be transferred to the heating zone, and wherein the dividing element does not allow permeation of gaseous components to and from the heating zone and said first reaction zone, and wherein the alkane feed passes through the heating zone and absorbs a sufficient amount of the heat produced in the first reaction zone to initiate the conversion of at least one alkane to an alkene in the second reaction zone; and (D) converting at least a portion of the alkane feed so as to form an alkene product.

57. The process of claim 56, further comprising feeding the first zone effluent to the second reaction zone.

58. The process of claim 56, wherein the first zone effluent comprises at least about 1,000 ppm oxygen.

59. The process of claim 56, wherein the first zone effluent comprises less than about 1,000 ppm oxygen.

60. The process of claim 56, wherein the alkane feed further comprises oxygen.

61. The process of claim 60, wherein the alkane feed comprises an alkane to oxygen molar ratio of from about 1.6:1 to about 10:1.

62. The process of claim 56, wherein the alkene product exits the heating zone of the second reaction zone and mixes with the first zone effluent to form a mixed product stream.

63. The process of claim 62, wherein the mixed product stream is fed to an alkene production catalyst bed.

64. The process of claim 63, wherein a supplemental oxygen stream is further fed to the alkene production catalyst bed.

65. The process of claim 56, wherein the fuel comprises hydrogen, carbon monoxide, C1–C4 alkanes, C1–C4 alkenes, naphtha, natural gas, syngas, or mixtures thereof.

66. The process of claim 24, wherein the alkane feed further comprises steam.

67. The process of claim 24, wherein the dividing element has the shape of a tube with a first surface area in contact with the first reaction zone and a second surface area in contact with the heating zone such that the first surface area and the second surface area are on opposite sides of the dividing element.

* * * * *